(12) United States Patent
Boggett et al.

(10) Patent No.: US 6,173,197 B1
(45) Date of Patent: Jan. 9, 2001

(54) APPARATUS FOR MEASURING MICROVASCULAR BLOOD FLOW

(75) Inventors: David Boggett, Devon; Xiabing Huang, Somerset, both of (GB)

(73) Assignee: Moor Instruments Limited, Devon (GB)

( * ) Notice: Under 35 U.S.C. 154(b), the term of this patent shall be extended for 0 days.

(21) Appl. No.: 09/297,728

(22) PCT Filed: Nov. 7, 1997

(86) PCT No.: PCT/GB97/03074

§ 371 Date: Jul. 9, 1999

§ 102(e) Date: Jul. 9, 1999

(87) PCT Pub. No.: WO98/20794

PCT Pub. Date: May 22, 1998

(30) Foreign Application Priority Data

Nov. 9, 1996 (GB) .................................................. 9623363

(51) Int. Cl.[7] .................................................. A61B 5/00
(52) U.S. Cl. ...................................... 600/310; 600/504
(58) Field of Search .................................. 600/310, 322, 600/473, 476, 504, 526

(56) References Cited

U.S. PATENT DOCUMENTS

| 4,590,948 | 5/1986 | Nilsson . |
| 4,596,254 | 6/1986 | Adrian et al. . |
| 4,862,894 | * 9/1989 | Fujii ..................................... 600/476 |
| 5,598,841 | 2/1997 | Taniji et al. . |

FOREIGN PATENT DOCUMENTS

WO 90/1104   10/1990   (WO) .

WO 91/06244   5/1991   (WO) .

OTHER PUBLICATIONS

B. Ruth, "Non–Contact Blood Flow Determination Using a Laser Speckle Method," *Optics and Laser Technology*, vol. 20, No. 6, Dec. 1988, Guildford, Surrey, Great Britain, pp. 309–316.

R. J. Gush, et al., "Investigation and Improved Performance of Optical Fibre Probes in Laser Doppler Blood Flow Measurement," *Medical & Biological Engineering & Computing*, vol. 25, No. 4, Jul. 1987, Stevenage, Herts, Great Britain, pp. 391–396.

* cited by examiner

Primary Examiner—Eric F. Winakur
(74) Attorney, Agent, or Firm—Barry R. Lipsitz

(57) ABSTRACT

An apparatus for measuring microvascular blood flow in tissue including a monochromatic light source arranged to irradiate a section of the tissue with the monochromatic light from the light source, a photodetector arranged to collect light scattered from the irradiated section, a processor for processing the electrical output signals from the photodetector, calculating the power spectrum of photocurrents generated in the detection of laser light scattered from static tissue and Doppler broadend laser light scattered from moving blood cells, and recording the average Doppler frequency shift, and further calculating and recording the blood concentration. The apparatus further measures and records the intensity of the detected scattered light, calculates and records the blood perfusion (flux), filters movement artefact noise, and displays the blood perfusion measured parameters. By filtering movement artefact noise, the apparatus enables fast tissue blood perfusion monitoring with enhanced signal quality.

12 Claims, 4 Drawing Sheets

APPARATUS FOR MEASURING MICROVASCULAR BLOOD FLOW

The present invention relates to an apparatus for measuring microvascular blood flow.

Blood flow in the small blood vessels of the skin performs an essential role in the regulation of the metabolic, hemodynamic and thermal state of an individual and the condition of the microcirculation over both long and short time periods can reflect the general state of health. The degree of blood perfusion in the cutaneous microvascular structure often provides a good indicator of peripheral vascular disease and reduction of blood flow in the microcirculatory blood vessels can often be attributed to cutaneous vascularisation disorders; so there are many situations in routine clinical medicine where measurement of the blood flow is important.

The microcirculation, its responses to stimuli, and its response to therapeutic regimes, were not open to routine continuous assessment and investigation until the introduction of the laser Doppler technique in the 1970's and subsequent developments in the 1980's.

The technique depends on the Doppler principle whereby laser light (which must be highly monochromatic and hence have a long coherence length) which is incident on tissue (typically the skin surface), is scattered by moving red blood cells and undergoes frequency broadening. The frequency broadened laser light, together with laser light scattered from static tissue, is photo detected and the resulting photo current processed to provide a signal which correlates with blood flow.

Laser light can be directed to the tissue surface either via an optic fibre or as a light beam. For "fibre optic" monitors the optic fibre terminates in an optic probe which can be attached to the tissue surface. One or more light collecting fibres also terminate in the probe head and these fibres transmit a proportion of the scattered light to a photo detector and the signal processing electronics. Normal fibre separations in the probe head are a few tenths of a millimeter so consequently blood flow is measured in a tissue volume of typically 1 mm$^3$ or smaller.

When a larger volume of tissue is stimulated to vasodilate or vasoconstrict, or where for example a healing process results in increased blood flow, the measured blood flow changes in the small tissue volume is generally taken to be representative of the larger volume.

For laser beam monitors single point measurements can be made by directing the beam to the desired point on the surface. By scanning the beam in a raster fashion a series of measurements can also be made, and by colour coding the flow measurements a colour image of blood flow distribution over the scanned surface can be displayed on a computer monitor screen.

Single point measurements give a high temporal resolution (40 Hz data rates are typical) enabling rapid blood flow changes to be recorded, whereas the laser Doppler imager can provide spatial information and has the ability to average blood flow measurements over large areas. Fibre optic systems can measure at tissue sites not easily accessible to a laser beam. For example measurements in brain tissue, mouth, gut, colon, muscle and bone.

Perfusion measurements using single and multiple channel fibre optic laser Doppler monitors have been made on practically all tissues and applied in most branches of medicine and physiology. The technique and its application has been described in numerous publications. A representative selection of these are included in "Laser-Doppler Blood Flowmetry", ed. A. P. Shepherd and P.Å. Oberg, Kluwer Academic Publishers 1990 and also "Laser Doppler", ed. G. V. Belcaro, U. Hoffmann, A. Bollinger and A. N. Nicolaides, Med-Orion Publishing Co. 1994.

The basic principles of measuring blood flow using coherent radiation and the Doppler effect were first described by C. Johnson in U.S. Pat. No. 3,511,227 patented May 12, 1970 entitled "Measurement of Blood Flow using Coherent Radiation and Doppler Effect".

The application of these principles to measurements in the microcirculation was described by M. D. Stern in "Nature", Vol 254, 56, March 1975, "In vivo evaluation of microcirculation by coherent light scattering"; M. D. Stern et al, 1977 "Continuous measurement of tissue blood flow by laser-Doppler spectroscopy", Am J. Physiol 232: H441–H448; and subsequent in U.S. Pat. No. 4,109,647, Aug. 29, 1978 "Method of and apparatus for Measurement of Blood Flow using Coherent Light".

An apparatus using fibre optics to transmit the laser light to tissue site and collect scattered light using one or more optic fibres was described by Holloway, G. A. and D. W. Watkins, 1977, "Laser Doppler measurement of cutaneous blood flow", J. Invest. Dermatology 69: 306–309 and D. W. Watkins and G. A Holloway, 1978, "An instrument to measure cutaneous blood flow using the Doppler shift of laser light", IEEE Trans Biomed Eng BME-25: 28–33. Extensions to theory and investigation of experimental models were made by R. Bonner and R. Nossal June 1981, Vol 20 No. 12, Applied Optics, "Model for laser Doppler measurements of blood flow in tissue". They showed that the first moment of the power spectral density of the photo current produced by the heterodyne mixing of Doppler shifted and unshifted laser light scattered from the microvasculature could be used as a measurement of perfusion. This parameter is commonly referred to as "Flux". They described the photon characteristics both in terms of auto correlation functions and spectral properties and used photo correlation techniques for their experimental investigations.

A perfusion monitor based on the application of auto correlation techniques is described by R. J. Adrian and J. A. Burgos "Laser Doppler flow monitor", U.S. Pat. No. 4,596, 254, Jun. 24, 1986.

In the present investigation we have used mainly digital signal processing but have chosen to use the technique of Fast Fourier Transformation, implemented with large scale digital signal processor (DSP) ICs, for the Flux calculations. This enables the high data rates necessary for real time graphical display.

The algorithms we have implemented have the important advantage that noise due to fibre movements, a major problem in existing laser Doppler fiber optic instruments, is generally reduced to insignificant levels. Using FFT processing with post DSP systems has additional advantages in that processing algorithms can be changed without a corresponding change in hardware. For example, the processing bandwidth for the Doppler shifts can be changed, measurements at different bandwidths can be done simultaneously; different frequency weighting in the "flux" calculation can be used to provide a means of easily differentiating fast from slow blood flows and hence provide a means of depth discrimination.

Reducing the use of analogue circuits to a minimum has the added advantages of greater reliability, reduced size and weight, and reduced manufacturing and servicing costs.

The present invention provides an apparatus for measuring blood in tissue comprising:

a monochromatic light source;

means for irradiating a section of the tissue with the monochromatic light from the light source;

means for collecting light scattered from the irradiated section;

means for photodetecting the collected scattered light;

means for processing the electrical output signals from the photodetector;

means for calculating the power spectrum of the photocurrents generated in the detection of laser light scattered from static tissue and Doppler broadened laser light scattered from moving blood cells;

means for calculating and recording the average Doppler frequency shift;

means for calculating and recording the blood concentration;

means for measuring and recording the intensity of the detected scattered light;

means for calculating and recording the blood perfusion (flux);

means for filtering movement artefact noise;

means for displaying the blood perfusion measured parameters.

Embodiments of the invention will now be described with reference to the accompanying drawings in which.

Figure 1:
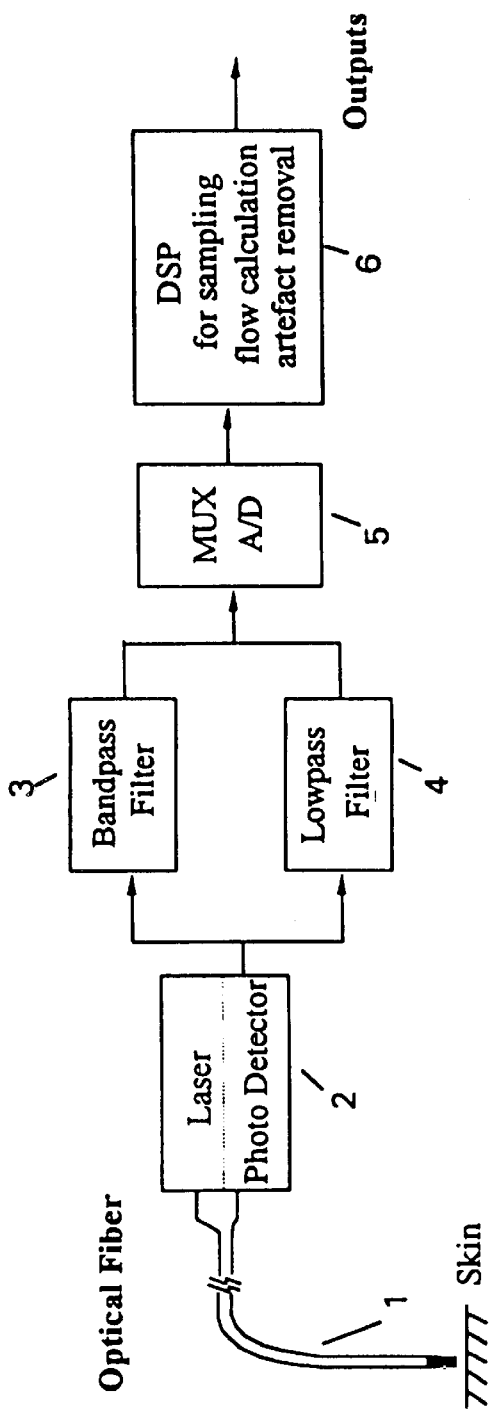
FIG. 1 is a block diagram of an apparatus for laser Doppler perfusion monitoring, said apparatus including a DSP for real-time flux calculation and removal of the fibre movement artefact in accordance with the invention.

As shown in FIG. 1, red or near infra-red light from a low power laser (2) is directed via an optical fibre (1) to the tissue and the light scattered back from the tissue is collected by one or more other optical fibres (1) and received by the photodetector (2). The photodetector converts the optical signal into an electrical signal. A bandpass filter (3) is used to remove noise outside the bandwidth and extract blood flow related AC components. A low-pass filter (4) is also connected to the output of the photodetector and is used to extract DC components proportional to the intensity of the collected light. Outputs of the bandpass (3) and low-pass filter (4) are converted into digital form by a multiplexer and A/D (5). Spectral analysis of the digitised Doppler signal, blood flow calculation and movement artefact detection and removal are performed by the powerful DSP device (6) in real-time.

FLOW CALCULATION

Laser light reflected and scattered from tissue consists of two fractions, one which is unchanged in frequency and one which has a Doppler broadened fraction due to interactions with moving blood cells in the microvasculature of the tissue. The performance of any laser Doppler flow monitor (LDF) mainly depends on the nature of the signal processing algorithm and the way of implementing the algorithm. Since the introduction of the first LDF monitor, many different methods of obtaining a reliable blood flow measurement have been proposed in the literature. Frequency weighting the detected signal, which essentially introduces a velocity-dependent multiplier into the signal processing, has become the most frequently used method for blood flow monitoring. This algorithm can be expressed by:

$$\omega \text{ weighting:Flux} = \int_{\omega_1}^{\omega_2} \omega P(\omega) d\omega$$

Other $\omega$ weightings can also be used. For example, an $\omega^2$ weighting will give increased weighting to scattering from fast moving red blood cells. The algorithm is:

$$\omega^2 \text{ weighting:Flux} = \int_{\omega_1}^{\omega_2} \omega^2 P(\omega) d\omega$$

where $\omega_1$ and $\omega_2$ are lower and upper cut-off frequencies of the bandpass filter, $P(\omega)$ is the power spectral density.

Because of the complicated and time consuming computation of a large number of power spectra, most LDFs adopt an analogue approach to implement the above processing, through Adrian et al (U.S. Pat. No. 4,596,254, Jun. 24, 1986) describe a digital processing technique which employs a simplified autocorrelation algorithm to achieve continuous and real-time computation of blood flow.

The recently available DSP devices can perform 1024 points FFT calculations within 10 ms, which makes it possible to compute flow output directly in frequency spectrum form as described in the $\omega$ and $\omega^2$ weighted algorithms. The present invention describes a method and apparatus to measure blood flow in real-time by using a DSP for digital processing of the power spectra of blood flow signal.

In digital form, the above weighting function can be written as:

$$\omega \text{ weighting:Flux} = \int_{\omega_1}^{\omega_2} \omega P(\omega) d\omega = \sum_{n_1}^{n_2} nP(n)$$

$$\omega^2 \text{ weighting:Flux} = \int_{\omega_1}^{\omega_2} \omega^2 P(\omega) d\omega = \sum_{n_1}^{n_2} n^2 P(n)$$

and noise subtracted and normalised forms $\text{Flux}_{sn}$ are $\omega$ weighting:$\text{Flux}_{sn} = (\Sigma nP(n) - \text{Noise})/DC^2$ $(\omega^2$ weighting:$\text{Flux}_{sn} = (\Sigma n^2 P(n) - \text{Noise})/DC^2$ Noise = SN×DC + DN where $n_1$ and $n_2$ are lower and upper limits of frequency components in the computation, $P(n)$ is the power spectra density of the nth frequency component, Noise is the system noise which includes dark noise (DN) and DC proportional shot noise (SN). DC is a measurement of the intensity of the collected scattered light.

Figure 2:
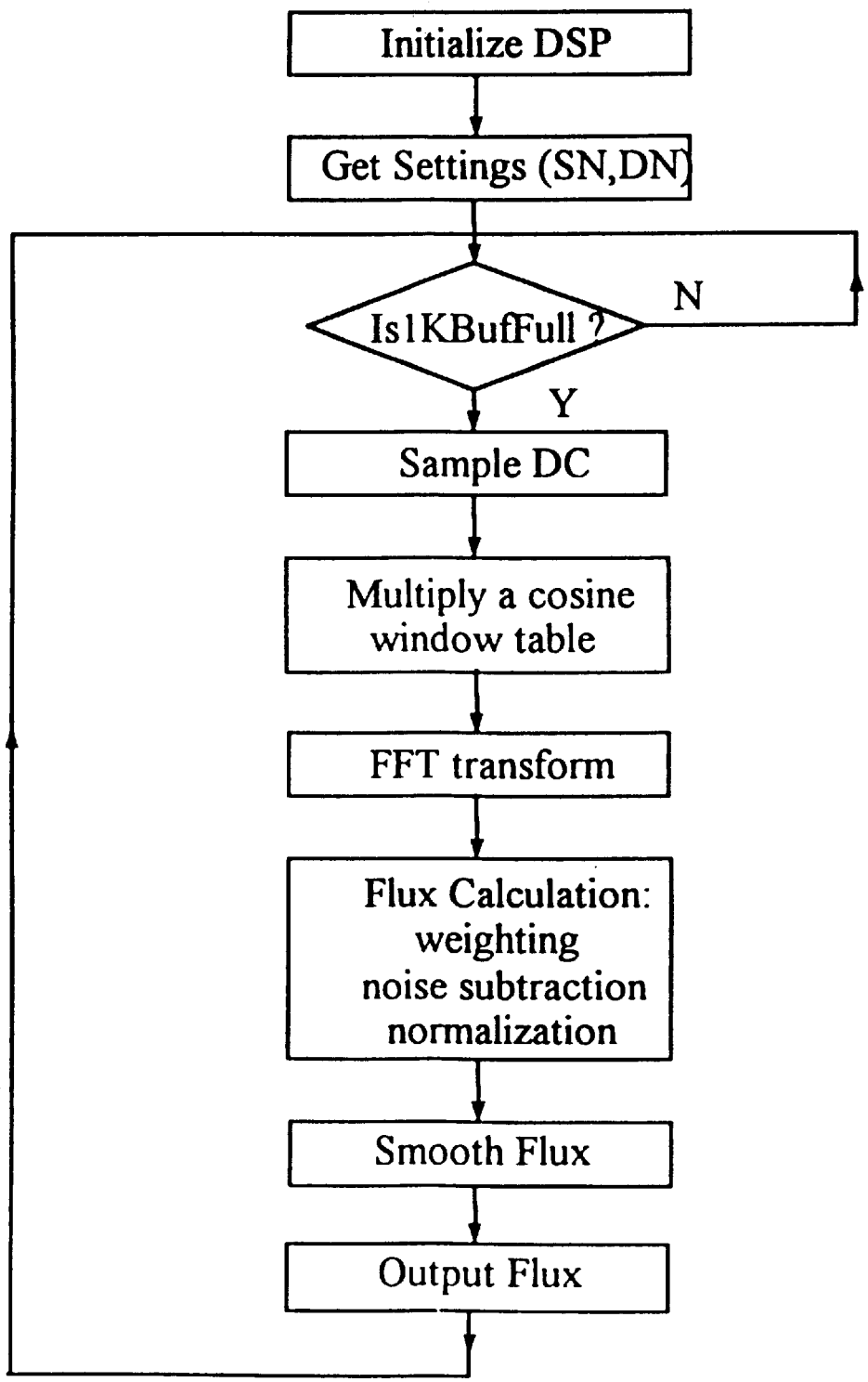
FIG. 2 is a flowchart of real-time FFT and flow calculation using DSP in accordance with the invention.

A detailed implementation of the above algorithms is illustrated in FIG. 2. As an example, the Doppler signal (AC) is sampled at 32 KHz and 1024-point FFT is used. When 1024 points of data are sampled, data is multiplied by a twiddle cosine window table to reduce artefactual spectral content resulting from discontinuities at the start and end points of the sampled wave form, and then is converted into frequency domain by FFT, and the weighting function, noise subtraction, normalisation and smoothing are performed by the DSP. After the FFT transformation of the 1024 points of data is completed, the DSP starts to sample the next 1024 points of Doppler signals so that a higher data rate can be achieved. The employed DSP system enables sampling and flux calculation to be performed in approximately 33 ms, so that a data rate of 30 Hz is possible.

Figure 3:
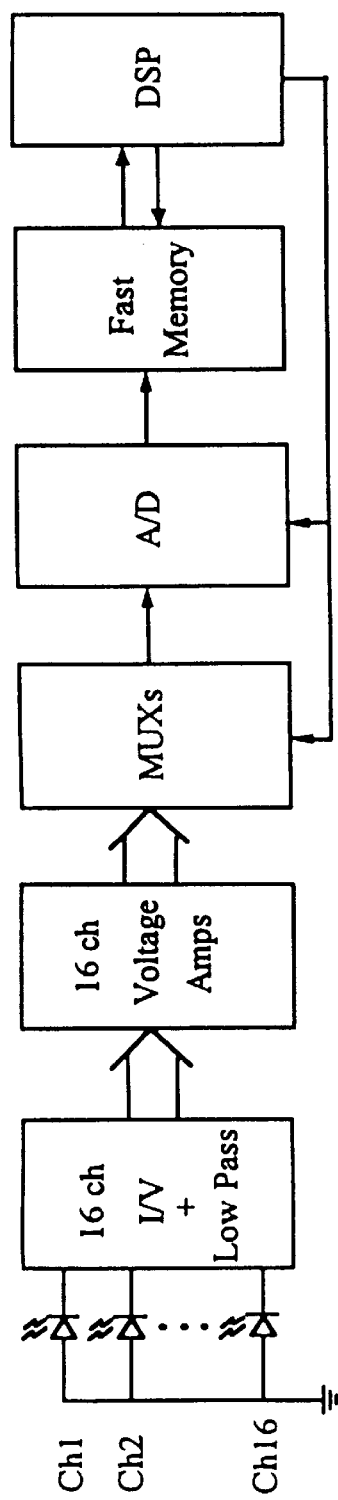
FIG. 3 is a flowchart of real-time FFT and flow calculation using DSP for a multichannel system in accordance with the invention.

FIG. 3 illustrates the use of a DSP in a multichannel system. This example is a 16 channel laser Doppler system which can achieve 10 Hz data rates for 256 point FFT's.

By the means of digital spectra processing of the Doppler signal described, a continuous blood flow output is produced. It is apparent that both $\omega$ and $\omega^2$ weighting or other spectra analysis algorithms can be easily implemented without significantly altering the concept involved. Also, different frequency ranges of the Doppler signal can be analysed separately by choosing the lower and upper limits of frequency components. For example, if it is known that blood flow signal for a particular application is toward high frequency band, low frequency components can be ignored by increasing the lower limit $n_1$ to produce less noise flow output. Another example is to calculate the ratio of flow from high frequency band and low frequency band using the present invention apparatus. Furthermore, other parameters, such as average velocity of the blood flow, concentration can be calculated in a similar way.

The average Doppler frequency shift $<\omega>$ of the light scattered from moving red blood cells is directly proportional to the average speed of these cells.

$$\langle \omega \rangle = \int_{\omega_1}^{\omega_2} \omega P(\omega) d\omega \bigg/ \int_{\omega_1}^{\omega_2} P(\omega) d\omega$$

Red blood cell (rbc) concentration is proportional to the integrated power spectral density for low concentration (less than 0.5%) i.e.

$$rbc \text{ concentration} \propto \int_{\omega_1}^{\omega_2} P(\omega) d\omega$$

MOVEMENT ARTEFACT

Movement artefact can be a major problem for the clinical use of a laser Doppler flow monitor based on fibre-optic transducers. Clinical studies often reveal changes in the blood flow signal which are unrelated to actual physiological changes in blood flow and are usually produced by movement of the optical fibres. Also when the means of tissue irradiation is via a laser beam relative movements of beam and tissue surface can produce noise components similar to those generated by fibre movement. In many applications of laser Doppler flow monitors, it is possible to ensure that a subject remains still during the measurement. However, this is not feasible in some conditions, such as cerebral perfusion monitoring, intrapartum monitoring or monitoring a baby. Although there has been a recent trend by many LDF equipment manufacturers to move to small diameter optical fibres in order to reduce movement artefact, the problem still persists. The commercially-available laser Doppler flow monitor known as Perimed PF3 employs an analogue circuit to reject movement artefact simply based on slope rate of the blood flow signal. If the rate of change of slope in the blood flow signal exceeds the likely physiological change, the output is switched off until such abrupt change has discontinued. However, when the fibre movements are small, the system finds it difficult to distinguish movement artefact from genuine changes in blood flow. Continuous fibre movement of large enough amplitude to trigger the rejection filter leads to a bizarre situation in which the blood flow output is unavailable during most of the recording period.

The present invention comprises a means of frequency analysis to detect movement artefact in real-time and a means to provide a continuous blood flow output even during fibre movement.

Figure 4:
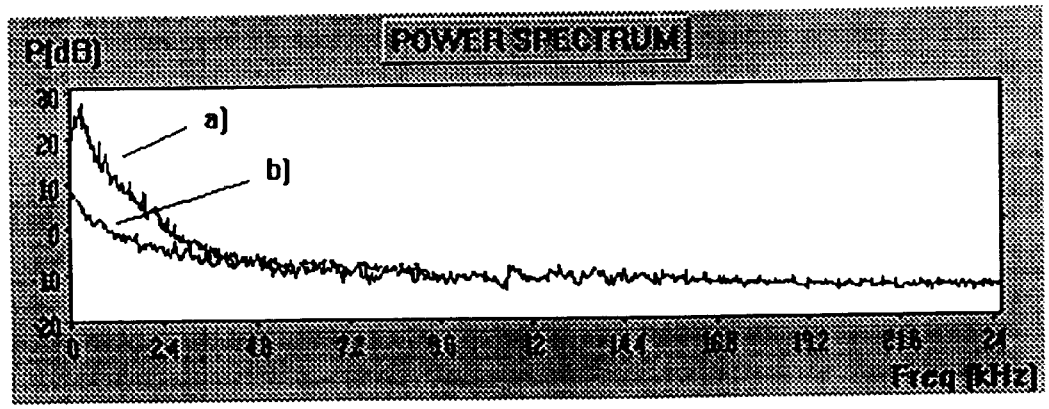
FIG. 4 shows the power spectra obtained from skin with and without fibre movement.

Fibre movement is known to produce an increase in the Doppler beat frequency spectrum and is generally considered to be the result of the changing modal interference pattern. For the purpose of identifying the frequencies influenced by the fibre movement, a set of experiments has been conducted in which the fibre was placed near a mechanical arm controlled by a DC motor and movement artefact was produced by driving the mechanical arm forwards and backwards to hit the fibre. FIG. 4 shows the power spectra obtained from skin with (a) and without (b) fibre movement. It can be seen that the effect of fibre movement was mainly confined to the lower part of the beat frequency spectrum associated with the blood flow signal, particularly below 3 KHz, and has less influence on the higher frequency range related to fast blood cells. Therefore, by calculating the change of the spectral power in a low frequency band (e.g. 20 Hz–3 KHz), it is possible to detect movement artefact which causes a sudden increase in the power density on the lower frequency range, while blood flow increases which mainly changes over higher frequency range will not be mis-detected as noise. With the use of DSP and the fast Fourier transformation, noise reduction algorithms can be easily implemented without any change to the hardware.

In an example of a noise reduction algorithm illustrated here, two parameters are calculated together with the blood flux. One is the current value of the $\omega$ weighted power density (LP) over the low frequency band (e.g. 20 Hz–3 KHz) and the other is the averaged $\omega$ weighted power density over this frequency band (LPA).

$$LP = \sum_{1}^{N} n \cdot P(n) \quad \text{and}$$

$$LPA = LPAold + (LP - LPAold) \times \alpha$$

where N is the number of Fourier components in the range 0 to 3 KHz and LPAold is the value of LPA previous to the calculation of LPA.

This equation describes low pass filtering of LP, to produce an averaged value, where $\alpha$ is a parameter inversely proportional to the time constant of the filter, i.e.

$$\alpha = \frac{1}{f_s} \times \frac{1}{TC}$$

where $f_s$ is the signal sample rate and TC is the time constant.

For example

For example $f_s = 30$Hz and $TC = 1.0$s $$\alpha = 0.033$$

LP is compared with LPA to determine whether or not LP has a significant noise content.

The time constant (TC) can be preset, or in some cases calculated automatically from spectra measured with and without noise induced, to suit the characteristics of the monitored blood flow signal. A long (TC), e.g. 1.0 s, will result in a relatively stable value for LPA so that sensitivity to a noisy LP value is high; however if the time constant is too long the noise filter could be triggered by a pulsatile flux signal which has its origins in a physiological change in addition to noise triggering. A fixed large TC is therefore suitable only when slow changes in blood flow are to be recorded, for example monitoring trends over minutes or hours. For monitoring fast changing flux changes e.g. changes associated with the cardiac cycle a short time constant e.g. TC=0.1 s is appropriate.

Triggering of the filter is set to occur when the LP exceeds LPA scaled by an appropriate coefficient i.e. triggering if LP>s×LPA Typically s has a value between 1.5 and 2.5.

A lower value could result in filtering out of a physiological change and a higher value may not filter out a noise signal.

For this present example filtering can be done in two ways. During the period for which LP>s×LPA either the noisy signal is replaced by relatively noise free data recorded in a period immediately prior to the noisy period (noise replacement filtering) or the noise is reduced by calculating the flux with the noisy LP value replaced by LPA. In this latter case the unnormalised flux is calculated as:

$$Flux = LPA + HP$$

where HP is the ω weighted power spectral density for the high frequency band e.g. 3 KHz to 15 KHz.

$$HP = \sum_{N}^{M} nP(n)$$

where N corresponds to 3 KHz and M to 15 KHz.

Figure 5:
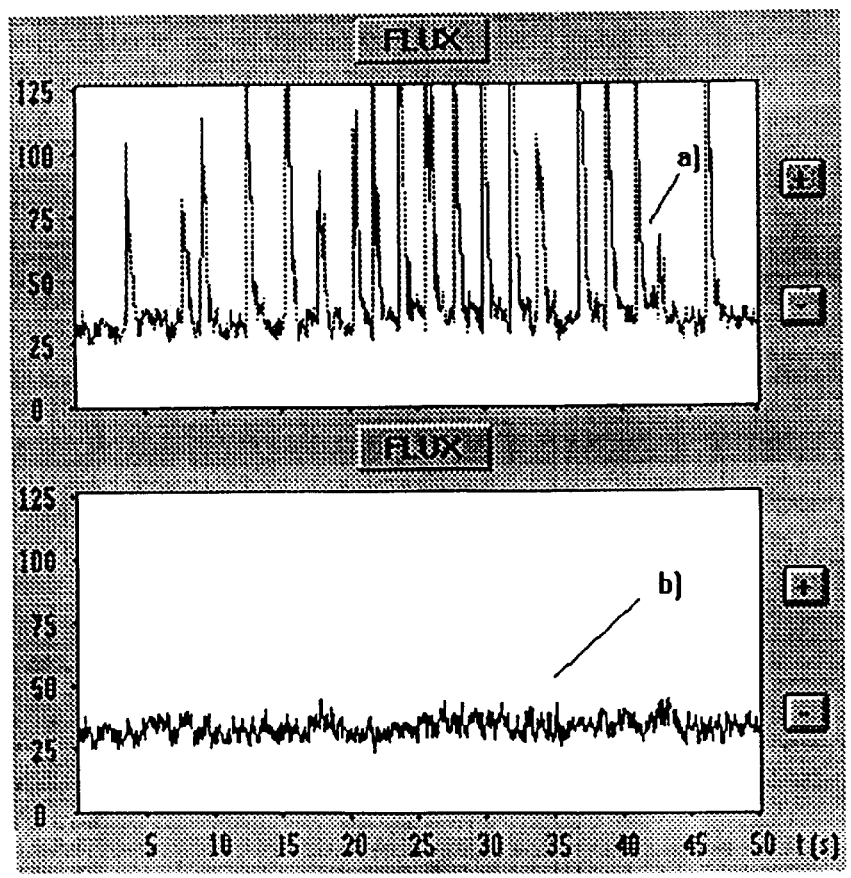
FIGS. 5–6 are two examples of blood flow outputs with and without fibre movement artefact removed using the apparatus of the present invention.

After movement artefacts are detected, in noise replacement filtering, a short period (for example 1 sec) "eye close" scheme is introduced, which is based on the fact that modal pattern fluctuations produced by a sudden short lived fibre movement will normally die out after a period of 1 second or less. During this period no further noise detection is performed and blood flow signal contaminated by the movement artefact will be replaced by the previous 1 sec of data which has been stored in the DSP. If the signal is still judged to be noisy at the end of the 1 second period, noise is again replaced by the earlier low noise signal. If pulsatile blood flow signal is monitored, the length of the "eye close" period can be changed according to the latest pulse rate, so one or more cycles of blood flow data can be used to replace the noise contaminated signal in order to retain the pulsatile nature. A measuring apparatus constructed in the afore described manner in accordance with the invention was evaluated. FIG. 5(a) illustrates a noisy signal (noise produced by fibre movement) measured from the Brownian motion of microspheres in water and FIG. 5(b) shows the recorded signal when the noise replacement filter is applied with a time constant of 0.5 s and a scaling coefficient of 2.0.

Figure 6:
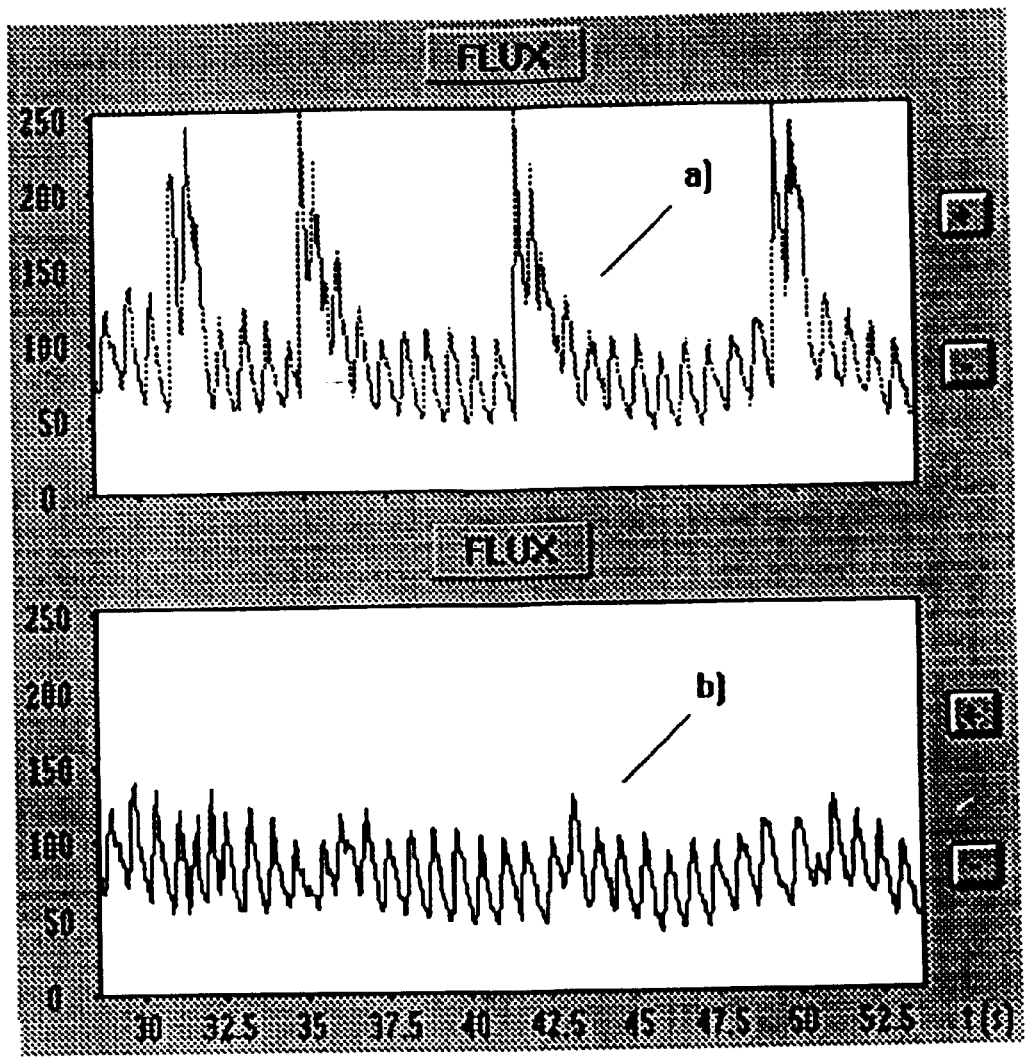

FIG. 6(a) illustrates a noisy signal measured from a finger tip. The flux is pulsatile, with a repetition rate equal to the volunteer's pulse rate.

FIG. 6(b) shows the recorded signal when the filter is applied with a time constant of 0.1 s, a scaling coefficient of 2.0, and noisy signals replaced by low noise pulsatile signals.

It is apparent that various changes and modifications, such as looking at different frequency ranges, employing a sophisticated adaptive threshold detection algorithm for noise detection, using averaged low frequency power spectra to replace noise contaminated signal over low frequency range can also be implemented.

Frequency ranges other than the 20 Hz–3 KHz can be used depending on the optic fibre type used, because in general the smaller the core diameter the smaller the frequency range of movement artefact noise signals. For example, a lower frequency band 20 Hz–1 KHz used with 50 micron core diameter fibre enables good discrimination between signal and noise.

For a measurement protocol where a very rapid increase in flux is predicted, (e.g. the release of a pressure cuff occluding or partially occluding blood flow into a limb) the algorithm applied in the filter example described will not be able to discriminate between movement artefact noise and signal. If this is so provision can be made to switch off the filter immediately prior to pressure release to enable the rapid flux change to be recorded.

The timing for the pressure release and the switching off of the filter can be pre-programmed to coincide if a suitable control program is available for the laser Doppler monitor or the filter can be turned off using a trigger signal from a pressure transducer.

The present invention provides an alternative to switching off the filter by applying algorithms which enable discrimination between noise signals and rapidly varying flux signals which have their origins in a physiological change. This requires both high (HPA) and low (LPA) frequency average ω weighted power density parameters to be calculated and comparisons to be made with their respective current values (HP) and (LP).

$$HPA = HPAold + (HP - HPAold) \times \alpha$$

the high frequency band equivalent of the LPA equation.

For a pressure cuff release resulting in reactive hyperaemia (generally a large increase in blood perfusion) both LP and HP will increase significantly whereas if the increase was due to noise only LP will significantly increase.

The noise filter is set to turn ON if:

LP>s×LPA and

HP<g HPA where g is a scaling coefficient value typically 1.5 to 2.5. This condition, a large increase in LP and a small or zero increase in HP, is characteristic of movement artefact signal noise.

The noise filter will not turn ON and hence the flux change will be recorded if:

HP>g HPA

The scaling coefficient can be automatically set by recording photocurrent spectra for fibre noise and for reactive hyperaemia, though because of possible non standard responses provision is made to switch off the noise filter manually or by using a trigger signal from a pressure transducer.

The relative changes in LP and HP can also be used in a direct way to discriminate between noisy and relatively noise free signals. The normal range LP/HP ratios from noise free signals can be recorded and used as reference levels so that abnormal LP/HP ratios are used to trigger ON the noise filter.

For blood perfusion recordings of trends over very long periods e.g. several hours very low data rates are appropriate for example 1 data point for each 10 second period. As noise always results in apparent signal increase and as movement artefact generated noise is seldom continuous an effective method of noise reduction in the recorded signal is to record the minimum detected signal level for each 10 second measurement period. A short time constant is used for the flux calculations to ensure that the effect of large noise signals in the flux calculation is short lived. During any 10 second period there is then a high probability of a signal sample taken in noise free (i.e. movement artefact noise free) conditions.

This filter has the advantage of simplicity and indeed does not require frequency analysis of the photocurrent for its implementation. Its disadvantage is that it is associated with a low data recording rate so that detail of events occurring within a sampling period is not recorded.

Filters which rely on the information derived from frequency analysis of the photocurrent spectra not only filter out a significant proportion of the noise signals but also enable high data recording rates to be implemented. Noise is filtered while at the same time information on changes in blood perfusion associated with the cardiac cycle, respiration, thermo regulation and vasomotion are recorded.

We claim:

1. An apparatus for measuring blood in tissue comprising:
   a monochromatic laser light source;
   means for irradiating a section of the tissue with the monochromatic light from the light source;
   means for collecting light scattered from the irradiated section;
   a photodetector fox detecting the collected scattered light;
   means for processing electrical output signals from the photodetector;
   means for calculating a power spectrum of photocurrents generated in the detection of laser light scattered from static tissue and Doppler broadened laser light scattered from moving blood cells;
   means for calculating and recording the average Doppler frequency shift;
   means for calculating and recording the red blood cell concentration;
   means for measuring and recording the intensity of the detected scattered light;
   means for calculating and recording the blood perfusion (flux);
   means for filtering movement artefact noise by measuring changes in the photocurrent power spectrum for a low frequency band;
   means for displaying the blood perfusion measured parameters;
   means to judge whether a change is due to movement artefact noise by comparison of current low frequency spectral power with averaged low frequency power or by comparison of current frequency weighted low frequency spectral power (LP) with the averaged frequency ($\omega$) weighted low frequency spectral power (LPA);
   means to calculate a blood perfusion (flux) value in the presence of detected movement artefact noise by summing the averaged frequency ($\omega$) weighted low frequency spectral power (LPA) with frequency weighted high frequency spectral power (HP), where:

Flux=Instrument Constant×(LPA+HP);

means to calculate a blood perfusion value in the absence of movement artefact noise by summing the current frequency weighted low frequency spectral power (LP) and the frequency weighted high frequency spectral power (HP), where:

Flux=Instrument Constant×(LP+HP);

and
   means to calculate a blood perfusion value in the presence of movement artefact noise comprising a noise replacement filter whereby during a noise affected period the noisy signal is replaced by noise free data recorded in a period immediately prior to the noisy period.

2. An apparatus according to claim 1, wherein the means for irradiating a section of tissue with monochromatic laser light is via an optic fibre and the means to collect light scattered from the tissue for photodetection is via one or more optic fibres.

3. An apparatus according to claim 1, wherein the means for irradiating a section of tissue with monochromatic laser light is with a laser beam.

4. An apparatus according to claim 1, wherein the signal frequency analysis, calculations of blood flow parameters and signal filtering to reduce the affects of movement artefact on the measured blood perfusion, red blood cell concentration and averaged Doppler frequency shift are carried out with the aid of fast large scale digital signal processing integrated circuits to enable real time processing and display.

5. An apparatus for measuring blood in tissue comprising:
   a monochromatic laser light source;
   means for irradiating a section of the tissue with the monochromatic light from the light source;
   means for collecting light scattered from the irradiated section;
   a photodetector for detecting the collected scattered light;
   means for processing electrical output signals from the photodetector;
   means for calculating a power spectrum of photocurrents generated in the detection of laser light scattered from static tissue and Doppler broadened laser light scattered from moving blood cells;
   means for calculating and recording the average Doppler frequency shift;
   means for calculating and recording the red blood cell concentration;
   means for measuring and recording the intensity of the detected scattered light;
   means for calculating and recording the blood perfusion (flux);
   means for filtering movement artefact noise by measuring changes in the photocurrent power spectra for both low and high frequency bands;
   means for displaying the blood perfusion measured paraeters;
   means to calculate frequency ($\omega$) weighted averaged spectral power for a low frequency band (LPA) and for a high frequency band (HPA);

means to judge whether changes are due to movement artefact noise by comparison of current frequency weighted low frequency spectral power (LP) with the averaged frequency weighted low frequency spectral power (LPA) and comparison of current frequency weighted high frequency spectral power (HP) with the averaged frequency weighted high frequency spectral power (HPA); and means to calculate a blood perfusion (flux) value in the presence of movement artefact noise detected by said comparison by summing the averaged frequency weighted low frequency spectral power (LPA) with the current frequency weighted high frequency spectral power (HP).

6. An apparatus according to claim 5, wherein the means for irradiating a section of tissue with monochromatic laser light is via an optic fibre and the means to collect light scattered from the tissue for photodetection is via one or more optic fibres.

7. An apparatus according to claim 5, wherein the means for irradiating a section of tissue with monochromatic laser light is with a laser beam.

8. An apparatus according to claim 5, wherein the signal frequency analysis, calculations of blood flow parameters and signal filtering to reduce the affects of movement artefact on the measured blood perfusion, red blood cell concentration and averaged Doppler frequency shift are carried out with the aid of fast large scale digital signal processing integrated circuits to enable real time processing and display.

9. An apparatus for measuring blood in tissue comprising:

a monochromatic laser light source;

means for irradiating a section of the tissue with the monochromatic light from the light source;

means for collecting light scattered from the irradiated section;

a photodetector for detecting the collected scattered light;

means for processing electrical output signals from the photodetector;

means for calculating the power spectrum of photocurrents generated in the detection of laser light scattered from static tissue and Doppler broadened laser light scattered from moving blood cells;

means for calculating and recording the average Doppler frequency shift;

means for calculating and recording the red blood cell concentration;

means for measuring and recording the intensity of the detected scattered light;

means for calculating and recording the blood perfusion (flux);

means for filtering movement artefact noise by sampling blood perfusion values at a rate comparable to the rate at which blood perfusion values are calculated;

means for displaying the blood perfusion measured parameters;

means to record the minimum perfusion value taken in a measurement period of long duration compared to the calculation period of the blood perfusion values and of short duration compared to the period for which the trend is to be recorded;

means to record minimum values for successive search periods; and means to display the blood perfusion minimum values for long measurement periods to produce trend records substantially free of movement artefact noise.

10. An apparatus according to claim 9, wherein the means for irradiating a section of tissue with monochromatic laser light is via an optic fibre and the means to collect light scattered from the tissue for photodetection is via one or more optic fibres.

11. An apparatus according to claim 9, wherein the means for irradiating a section of tissue with monochromatic laser light is with a laser beam.

12. An apparatus according to claim 9, wherein the signal frequency analysis, calculations of blood flow parameters and signal filtering to reduce the affects of movement artefact on the measured blood perfusion, red blood cell concentration and averaged Doppler frequency shift are carried out with the aid of fast large scale digital signal processing integrated circuits to enable real time processing and display.

* * * * *